United States Patent
Jakobsen et al.

(10) Patent No.: US 8,828,677 B2
(45) Date of Patent: Sep. 9, 2014

(54) PROTEASE CRYSTALS IN BROTH

(75) Inventors: Sune Jakobsen, Vaerloese (DK); Kim Uhre Hansen, Kalundborg (DK); Svend Kaasgaard, Skovlunde (DK)

(73) Assignee: Novozymes A/S, Bagsvaerd (DK)

( * ) Notice: Subject to any disclaimer, the term of this patent is extended or adjusted under 35 U.S.C. 154(b) by 1140 days.

(21) Appl. No.: 12/044,064

(22) Filed: Mar. 7, 2008

(65) Prior Publication Data

US 2008/0227175 A1    Sep. 18, 2008

Related U.S. Application Data

(60) Provisional application No. 60/895,203, filed on Mar. 16, 2007.

(30) Foreign Application Priority Data

Mar. 15, 2007  (EP) .................................... 07104220

(51) Int. Cl.
   *C12Q 1/37*    (2006.01)

(52) U.S. Cl.
   USPC ................................. 435/23; 435/4

(58) Field of Classification Search
   USPC ....................................... 435/23, 4
   See application file for complete search history.

(56) References Cited

U.S. PATENT DOCUMENTS

| | | | |
|---|---|---|---|
| 5,340,926 A | 8/1994 | Lowe et al. | |
| 6,316,240 B1 | 11/2001 | Laustsen | |

FOREIGN PATENT DOCUMENTS

| | | |
|---|---|---|
| EP | 0574050 | 12/1993 |
| JP | 4066086 A | 3/1992 |
| WO | WO 97/23604 | 7/1997 |

OTHER PUBLICATIONS

Kembhavi et al. "Salt-tolerant and thermostable alkaline protease from *Bacillus subtilis* NCIM No> 64", Applied Biochem. & Biotechno., 1993, 38:83-92.*
Cho et al. "Purification and characterization of protease from *Bacillus amyloliquefaciens* isolated from tranditional soybean fermentation starter", J. Agric. Food Chem., 2003, 51:7664-7670.*
Pearson et al. "Extracellular enzyme loss during polyelectrolyte flocculation of cells from fermentation broth", Biotechnology & Bioengineering, 2004, 87(1):61-68.*
Alexander et al, 2001, Biochem 40, 10634-10639.
Inoue et al, 1998, Biotechnol Appl Biochem 28, 207-213.
Okumura et al, 2006, Protein Express Purification 47, 144-151.
Sassenfeld et al, 1990, Tibtech 8,88-93.
Wan et al, 1995, Biochem Mol Biol Intl 35(4), 899-912.

* cited by examiner

*Primary Examiner* — Bin Shen
(74) *Attorney, Agent, or Firm* — Michael W. Krenicky

(57) ABSTRACT

A method of solubilizing protease crystals and/or protease precipitate in a fermentation broth comprising a) diluting the fermentation broth 100-2000% (w/w);
b) adding a divalent salt; and
c) adjusting the pH value of the fermentation broth to a pH value below pH 5.5.

30 Claims, No Drawings

PROTEASE CRYSTALS IN BROTH

CROSS REFERENCE TO RELATED APPLICATIONS

This application claims priority or the benefit under 35 U.S.C. 119 of European application no. 07104220.4 filed Mar. 15, 2007 and U.S. provisional application No. 60/895,203 filed Mar. 16, 2007, the contents of which are fully incorporated herein by reference.

FIELD OF INVENTION

The present invention provides an improved method of solubilizing protease crystals and/or protease precipitate in a fermentation broth.

BACKGROUND

The fermentation yield of industrial proteases has increased dramatically over the passed years. The yield is now so high that more than 60% of the protease in the fermentation broth may be present as crystals and/or precipitate.

A number of methods have been applied for solving or minimizing this problem, see e.g., U.S. Pat. No. 6,316,240, wherein the pH of the culture broth is adjusted to a pH between 9.5 and 13.0.

SUMMARY OF THE INVENTION

The present inventors have found that it is possible to solubilize more than 80% of the protease crystals and/or protease precipitate in a fermentation broth, so we claim:

A method of solubilizing protease crystals and/or protease precipitate in a fermentation broth comprising
a) diluting the fermentation broth 100-2000% (w/w);
b) adding a divalent salt; and
c) adjusting the pH value of the fermentation broth to a pH value below pH 5.5.

DETAILED DESCRIPTION

Proteases

Protease crystals and/or protease precipitate and/or protease bound to cell mass/insolubles in a fermentation broth may be solubilized according to the present invention. In a preferred embodiment the protease is a subtilisin.

A subtilisin is a serine protease that uses a catalytic triad composed of Asp32, His64 and Ser221 (subtilisin BPN' numbering). It includes any enzyme belonging to the NC-IUBMB enzyme classification: EC 3.4.21.62.

A subtilisin may according to the peptidase classification be described as: clan SB, family S8, MEROPS ID: S08.001.

Subtilisins are described in, e.g., Barrett et al. 1998. Handbook of proteolytic enzymes. Academic press, p. 289-294.

The protease activity can be measured using any assay, in which a substrate is employed, that includes peptide bonds relevant for the specificity of the protease in question. Assay-pH and assay-temperature are likewise to be adapted to the protease in question.

There are no limitations on the origin of the protease of the invention and/or for the use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e.g., by Site-directed Mutagenesis, by PCR (using a PCR fragment containing the desired mutation as one of the primers in the PCR reactions), or by Random Mutagenesis. The preparation of consensus proteins is described in, e.g., EP 897985.

A preferred subtilisin is a subtilisin selected from the group consisting of subtilisin Carlsberg, subtilisin BPN', subtilisin 147, subtilisin 309 and subtilisin I168.

Preferred commercially available subtilisins include ALCALASE™, SAVINASE™, ESPERASE™, EVERLASE™, OVOZYME™, CORONASE™, POLARZYME™, and KANNASE™ (Novozymes A/S); MAXATASE™, MAXACAL™, MAXAPEM™, PROPERASE™, PURAFECT™, PURAFECT OXP™, FN2™, FN3™, and FN4™ (Genencor International Inc.); and BLAP X™ (Henkel).

It is known that many proteases, especially subtilisins, are unstable at low pH (below pH 5.5, in particular below pH 5.0). This fact makes the present invention so surprising: The pH of the fermentation broth comprising the protease crystals and/or the protease precipitate of interest is adjusted to a pH value below pH 5.5, and a 100% recovery is achieved (see Example 1, where there is a 100% activity in the supernatant at pH 4.5, and in Example 2, where there is a 100% activity in the supernatant at pH 4.2).

Microorganisms

The protease according to the invention may be obtained from a microorganism.

The microorganism may be a unicellular microorganism, e.g., a prokaryote, or a non-unicellular micro-organism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp.

In a preferred embodiment, the bacterial host cell is a *Bacillus lentus* cell, a *Bacillus licheniformis* cell, a *Bacillus stearothermophilus* cell or a *Bacillus subtilis* cell.

The microorganism may be a fungal cell. "Fungi" as used herein includes the phyla Ascomycota, Basidiomycota, Chytridiomycota, and Zygomycota as well as the Oomycota and all mitosporic fungi. Representative groups of Ascomycota include, e.g., *Neurospora, Eupenicillium* (=*Penicillium*), *Emericella* (=*Aspergillus*), *Eurotium* (=*Aspergillus*), and the true yeasts listed below. Examples of Basidiomycota include mushrooms, rusts, and smuts. Representative groups of Chytridiomycota include, e.g., *Allomyces, Blastocladiella, Coelomomyces*, and aquatic fungi. Representative groups of Oomycota include, e.g., Saprolegniomycetous aquatic fungi (water molds) such as *Achlya*. Examples of mitosporic fungi include *Aspergillus, Penicillium, Candida*, and *Alternaria*. Representative groups of Zygomycota include, e.g., *Rhizopus* and *Mucor*.

The fungal host cell may be a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g., genera *Kluyveromyces, Pichia*, and *Saccharo-

*myces*). The basidiosporogenous yeasts include the genera *Leucosporidim, Rhodosporidium, Sporidiobolus, Filobasidium,* and *Filobasidiella*. Yeasts belonging to the Fungi Imperfecti are divided into two families, Sporobolomycetaceae (e.g., genera *Sporobolomyces* and *Bullera*) and Cryptococcaceae (e.g., genus *Candida*).

In another embodiment, the fungal host cell is a filamentous fungal cell.

The host cell may also be a eukaryote, such as a mammalian cell, an insect cell, or a plant cell.

Fermentation Broth

The present invention may be useful for any fermentation in industrial scale, e.g., for any fermentation having culture media of at least 50 liters, preferably at least 500 liters, more preferably at least 5,000 liters, even more preferably at least 50,000 liters.

The microorganism producing the protease of interest may be fermented by any method known in the art. The fermentation medium may be a minimal medium as described in, e.g., WO 98/37179, or the fermentation medium may be a complex medium comprising complex nitrogen and carbon sources, wherein the complex nitrogen source may be partially hydrolysed as described in WO 2004/003216.

The fermentation may be performed as a batch, a repeated batch, a fed-batch, a repeated fed-batch or a continuous fermentation process.

In a fed-batch process, either none or part of the compounds comprising one or more of the structural and/or catalytic elements is added to the medium before the start of the fermentation and either all or the remaining part, respectively, of the compounds comprising one or more of the structural and/or catalytic elements are fed during the fermentation process. The compounds which are selected for feeding can be fed together or separate from each other to the fermentation process.

In a repeated fed-batch or a continuous fermentation process, the complete start medium is additionally fed during fermentation. The start medium can be fed together with or separate from the structural element feed(s). In a repeated fed-batch process, part of the fermentation broth comprising the biomass is removed at regular time intervals, whereas in a continuous process, the removal of part of the fermentation broth occurs continuously. The fermentation process is thereby replenished with a portion of fresh medium corresponding to the amount of withdrawn fermentation broth.

In a preferred embodiment of the invention, a fed-batch fermentation process is preferred.

Solubilizing Process

The method of the invention may be applied to an untreated fermentation broth or to a fermentation broth that has first been subjected to, but not limited to, e.g., a temperature adjustment, but before removal of cells and other solids. Accordingly, we also claim:

A method of solubilizing protease crystals and/or protease precipitate in a fermentation broth comprising
a) diluting the fermentation broth 100-2000% (w/w);
b) adding a divalent salt;
c) adjusting the pH value of the fermentation broth to a pH value below pH 5.5; and
d) removing the microorganism producing the protease of interest.

The fermentation broth comprising the protease crystals and/or the protease precipitate and/or the protease bound to cell mass/insolubles is according to the present invention diluted 100-2000% (w/w), preferably 100-1500% (w/w), more preferably 100-1000% (w/w), in particular 200-700% (w/w).

The dilution medium will typically be water, an ultrafiltration permeate from the protease process in question, a recycle of water from the protease process in question, a condensate from a heater, or any combination of the above mentioned, e.g., a mixture of water and the ultrafiltration permeate.

It has been found that a divalent salt is a surprisingly good solubilizing agent, in particular a calcium and/or a magnesium salt. A preferred divalent salt is a phosphate, a sulphate, a nitrate, an acetate, a chloride, e.g., calcium chloride or magnesium chloride. A preferred embodiment is a calcium salt.

The divalent salt should be added at a concentration of at least 0.01-5% of the diluted fermentation broth (w/w), in particular 0.01-1% of the diluted fermentation broth (w/w).

The dosage of the divalent salt is typically done either in-line, or in a mixing tank, or by any other method known in the art.

It may be an advantage, in addition to the divalent salt, to add one or more coagulating agents such as an aluminate, e.g., NaAlO2, and/or a cationic polymer, and/or an anionic polymer.

The pH of the fermentation broth is adjusted to a pH value below pH 5.5, in particular to a pH value below 5.0. The pH adjustment may be done before, simultaneously or after the addition of the divalent salt. The pH may be adjusted to a pH value between 2.0 and 5.5; preferably to a pH value between 2.0 and 5.0; more preferably to a pH value between 3.0 and 5.0, and in particular to a pH value between 4.0 and 5.0.

It is to be noted that the process steps of the invention:
a) diluting the fermentation broth 100-2000% (w/w),
b) adding a divalent salt, and
c) adjusting the pH value of the fermentation broth to a pH value below pH 5.5, may be done in any order; e.g., step a) and step b) may be performed simultaneously; step b) and step c) may be performed simultaneously; and step c) may be performed before step b).

The conductivity of the diluted fermentation broth (after the addition of the divalent salt and the pH adjustment) is preferably in the range of from 1 mS/cm to 100 mS/cm; more preferably in the range of from 1 mS/cm to 40 mS/cm; and in particular in the range of from 3 mS/cm to 20 mS/cm. The conductivity may, e.g., be monitored with a conductivity meter.

The diluted fermentation broth will typically have a temperature of from 5° C. to 50° C. It may be an advantage to heat the fermentation broth before, simultaneously or after the dilution, or to heat the fermentation broth before, simultaneously or after the addition of the divalent salt/pH adjustment.

After adding the divalent salt and adjusting the pH, a mixing will take place. The mixing time will depend on the chosen temperature and the crystal morphology of the protease in question.

More than 80% of the protease crystals and/or protease precipitate and/or protease bound to cell mass/insolubles may be solubilized according to the present invention; preferably more than 85% of the protease crystals and/or protease precipitate and/or protease bound to cell mass/insolubles may be solubilized; more preferably more than 90% of the protease crystals and/or protease precipitate and/or protease bound to cell mass/insolubles may be solubilized; and in particular more than 95% of the protease crystals and/or protease precipitate and/or protease bound to cell mass/insolubles may be solubilized.

After the solubilizing process described above the microorganisms are removed by methods known in the art such as, but not limited to, filtration, e.g. drum filtration, membrane filtration, or centrifugation.

It is to be noted that one of the important parameters in the recovery of a protease product from a culture broth containing the protease of interest in a partly crystalline or precipitated form is of course the overall extraction yield.

Under certain conditions, the recovery can be seen as a two step process, a first step where the protease is brought on a fully soluble form, and a second step where the protease is separated from the cell mass and other insolubles, commonly known as sludge. In the second step binding of the protease to the sludge will have a negative impact on the overall extraction yield. Unfortunately, the conditions favoring a fast dissolution of crystalline or precipitated enzyme, may increase the binding of the enzyme to the sludge.

However, by employing a specific embodiment of the invention, this problem can be solved by first dissolving the crystalline or precipitated protease by adjusting the pH of the fermentation broth to a value below 5.5, keeping the conductivity low (less than 20 mS/cm; in particular less than 15 mS/cm).

After the solubilization of the protease crystals and the protease precipitate the divalent salt is added to reduce the binding of the protease to the sludge. The conductivity will now be in the range of from 1 mS/cm to 100 mS/cm; more preferably in the range of from 1 mS/cm to 40 mS/cm; and in particular in the range of from 3 mS/cm to 20 mS/cm. The protease will now be in solution, and the protease can be separated from the sludge material by centrifugation, filtration, or other known separation processes.

In a further embodiment a small delay of from 20 seconds to 60 minutes between the dissolution step and the addition of the divalent salt is introduced, preferably a delay of from 20 seconds to 45 minutes between the dissolution step and the addition of the divalent salt is introduced; and in particular a delay of from 20 seconds to 30 minutes between the dissolution step and the addition of the divalent salt is introduced. The dissolution is a relatively slow process. According to the details given above we also claim:
A method of solubilizing protease crystals and/or protease precipitate and/or protease bound to cell mass/insolubles in a fermentation broth comprising
a) diluting the fermentation broth 100-2000% (w/w);
b) adjusting the pH value of the fermentation broth to a pH value below pH 5.5; and
c) adding a divalent salt, wherein there is a delay of from 20 seconds to 60 minutes between step b) and step c).

It is to be noted that the liberation of the protease from the sludge by addition of the divalent salt is a fast process, meaning that there is often no need for a delay before separating the protease from the sludge fraction by, e.g., centrifugation or filtration.

The two step process with a delay between step b) and step c) may advantageously be applied when the protease has a strong net positive charge at the pH used in the recovery process and the sludge has a net negative surface charge.

Subsequent Downstream Operations

The resulting protease may be further isolated by methods known in the art. For example, the protease may be recovered by conventional procedures including, but not limited to, further filtration, e.g., ultra-filtration and micro-filtration, extraction, spray-drying, evaporation, precipitation or crystallization.

The invention is further illustrated in the following examples which are not intended to be in any way limiting to the scope of the invention as claimed.

EXAMPLE 1

Ph and Calcium Effect on Solubilizing Protease (Subtilisin 309) Crystals

Subtilisin: The subtilisin was subtilisin 309 as described in EP 0396 608 B1.
Bacillus species: The Bacillus species was Bacillus licheniformis with copies of the subtilisin inserted as described in WO 02/00907.
Solubilizing Process:
The fermentation broth had a pH of 6.8.
The fermentation broth was diluted with water 300% (w/w) meaning that 1 kg of fermentation broth (culture broth =CB) was diluted with 3 kg of water.

8 samples were taken out. In 4 of the samples no calcium was added. In the other 4 samples 3% (w/w) of CaCl2 (36% (w/w)) relative to the undiluted fermentation broth was added meaning that the concentration of the divalent salt relative to the diluted fermentation broth was:

$$[(3 \times 0.36)/4]\% = 0.27\%.$$

pH was adjusted to 10.5; 7.5; 7.0; and 4.5.
All samples were mixed at room temperature for 1 hour except the samples with pH 7.

The samples were then centrifugated and the protease activity in the centrifugate was determined.

The results are shown in Table 1 below.

| | CB | Dilution | CaCl2 (36%) [% wt/CB] | pH | Time [minutes] | |
|---|---|---|---|---|---|---|
| | | | | | | Activity |
| Sample 1* | 100 | 0 | 0 | 7 | NA | 100% |
| | | | | | | Activity in the supernatant |
| | 100 | 300 | 0 | 4.5 | 60 | 45% |
| | 100 | 300 | 0 | 7 | 0 | 53% |
| | 100 | 300 | 0 | 7.5 | 60 | 64% |
| | 100 | 300 | 0 | 10.5 | 60 | 66% |
| | 100 | 300 | 3 | 4.5 | 60 | 100% |
| | 100 | 300 | 3 | 7 | 0 | 63% |
| | 100 | 300 | 3 | 7.5 | 60 | 79% |
| | 100 | 300 | 3 | 10.5 | 60 | 65% |

Sample 1*: All protease activity (from precipitate and centrifugate) was measured and set to 100%.

It can be seen from Table 1 above that if no calcium is added the protease activity in the centrifugate will decrease at lower pH: The protease activity at pH 10.5 is 66%; at pH 7.5 the activity is 64%; and at pH 4.5 the activity is 45%.

If the calcium salt is added the protease activity in the centrifugate will increase significantly with a lower pH: The protease activity at pH 10.5 is 65%; at pH 7.5 the activity is 79%; and at pH 4.5 the activity is 100%.

It is to be noted that at pH 10.5 there is no effect of the calcium addition.

EXAMPLE 2

Ph and Calcium Effect on Solubilizing Protease (Subtilisin 309 Variant) Crystals Subtilisin: The subtilisin was a variant of subtilisin 309 as described in WO 00/37599.

Bacillus species: The *Bacillus* species was *Bacillus licheniformis* with copies of the subtilisin inserted as described in WO 02/00907.

Solubilizing Process:

The fermentation broth had a pH of 7.4.

The fermentation broth was diluted with water 300% (w/w) meaning that 1 kg of fermentation broth (culture broth=CB) was diluted with 3 kg of water.

8 samples were taken out. In 4 of the samples no calcium was added. In the other 4 samples 3% (w/w) of CaCl2 (36% (w/w)) relative to the undiluted fermentation broth was added meaning that the concentration of the divalent salt relative to the diluted fermentation broth was:

$$[(3 \times 0.36)/4]\% = 0.27\%.$$

pH was adjusted to 10.5; 7.5; 7.0; and 4.2.

All samples were mixed at room temperature for 1 hour except the samples with pH 7.

The conductivity of the 8 samples was measured. They were all in the range of from 10.5 to 14.3 mS/cm.

The samples were then centrifugated and the protease activity in the centrifugate was determined.

The results are shown in Table 2 below.

|   | CB | Dilution | CaCl2 (36%) [% wt/CB] | pH | Time [minutes] |   |
|---|---|---|---|---|---|---|
|   |   |   |   |   |   | Activity |
| Sample 1* | 100 | 0 | 0 | 7 | 0 | 100% |
|   |   |   |   |   |   | Activity in the supernatant |
|   | 100 | 300 | 0 | 4.2 | 60 | 67% |
|   | 100 | 300 | 0 | 7 | 0 | 63% |
|   | 100 | 300 | 0 | 7.5 | 60 | 39% |
|   | 100 | 300 | 0 | 10.5 | 60 | 19% |
|   | 100 | 300 | 3 | 4.2 | 60 | 100% |
|   | 100 | 300 | 3 | 7 | 0 | 48% |
|   | 100 | 300 | 3 | 7.5 | 60 | 65% |
|   | 100 | 300 | 3 | 10.5 | 60 | 10% |

Sample 1*: All protease activity (from precipitate and centrifugate) was measured and set to 100%.

It can be seen from Table 2 above that if the calcium salt is added the protease activity in the centrifugate will increase significantly with a lower pH: The protease activity at pH 10.5 is 10%; at pH 7.5 the activity is 65%; and at pH 4.2 the activity is 100%.

It is to be noted that at pH 10.5 there is a negative effect of the calcium addition.

The invention claimed is:

1. A method of solubilizing protease crystals and/or protease precipitate in a fermentation broth comprising: a) providing a fermentation broth with protease crystals and/or protease precipitate;
b) diluting the fermentation broth 100-2000% (w/w);
c) adding a divalent salt; and
d) adjusting the pH value of the fermentation broth to a pH value below pH 5.5, wherein protease crystals and/or protease precipitate are dissolved into the fermentation broth.

2. The method according to claim 1, wherein the protease crystals and/or the protease precipitate are obtained from a microorganism.

3. The method according to claim 2, wherein the microorganism is a prokaryote or a eukaryote.

4. The method according to claim 2, wherein the prokaryote is a *Bacillus* cell.

5. The method according to claim 1, wherein the protease is a subtilisin.

6. The method according to claim 1, wherein the fermentation broth is diluted with water.

7. The method according to claim 6, wherein the fermentation broth is diluted with an ultrafiltration permeate.

8. The method according to claim 1, wherein the dilution is performed with a mixture of water and ultrafiltration permeate.

9. The method according to claim 1, wherein the divalent salt is a calcium salt and/or a magnesium salt.

10. The method according to claim 1, wherein the divalent salt is added at a concentration of 0.01-5% relative to the diluted fermentation broth.

11. The method according to claim 1, wherein the pH is adjusted to a pH between 2.0 and 5.0.

12. The method according to claim 11, wherein the fermentation broth is adjusted to a pH between 3.0 and 5.0.

13. The method according to claim 12, wherein the fermentation broth is adjusted to a pH between 4.0 and 5.0.

14. The method according to claim 1, wherein the fermentation broth has a temperature of from 5° C. to 50° C.

15. The method according to claim 1, wherein additionally one or more other flocculating agents are added to the fermentation broth.

16. The method according to claim 1, wherein step b) and step c) are performed simultaneously.

17. The method according to claim 1, wherein step c) and step d) are performed simultaneously.

18. The method according to claim 1, wherein step d) is performed before step c).

19. The method according to claim 1, wherein the conductivity is in the range of from 1 mS/cm to 100 mS/cm after steps b), c), and d).

20. The method according to claim 1, wherein more than 80% of protease crystals and/or protease precipitate and/or protease bound to cell mass/insolubles are solubilized.

21. The method of claim 1, wherein more than 80% of the protease crystals and/or protease precipitate are dissolved into the fermentation broth.

22. The method of claim 1, wherein more than 85% of the protease crystals and/or protease precipitate are dissolved into the fermentation broth.

23. The method of claim 1, wherein more than 90% of the protease crystals and/or protease precipitate are dissolved into the fermentation broth.

24. The method of claim 1, wherein more than 95% of the protease crystals and/or protease precipitate are dissolved into the fermentation broth.

25. A method of solubilizing protease crystals and/or protease precipitate and/or protease bound to cell mass/insolubles in a fermentation broth comprising:
a) providing a fermentation broth with protease crystals and/or protease precipitate and/or protease bound to cell mass/insolubles;
b) diluting the fermentation broth 100-2000% (w/w);

c) adjusting the pH value of the fermentation broth to a pH value below pH 5.5; and
d) adding a divalent salt, wherein there is a delay of 20 seconds to 60 minutes between step c) and step d), wherein the protease crystals and/or protease precipitate are dissolved into the fermentation broth.

26. The method of claim 25, wherein more than 80% of the protease crystals and/or protease precipitate are dissolved into the fermentation broth.

27. The method of claim 25, wherein more than 85% of the protease crystals and/or protease precipitate are dissolved into the fermentation broth.

28. The method of claim 25, wherein more than 90% of the protease crystals and/or protease precipitate are dissolved into the fermentation broth.

29. The method of claim 25, wherein more than 95% of the protease crystals and/or protease precipitate are dissolved into the fermentation broth.

30. A recovery method of solubilizing protease crystals and/or protease precipitate comprising:
   a) providing a fermentation broth with protease crystals and/or protease precipitate;
   b) diluting the fermentation broth 100-2000% (w/w);
   c) adding a divalent salt;
   d) adjusting the pH value of the fermentation broth to a pH value below pH 5.5;
   e) recovering solubilized protease crystals, solubilized protease precipitate, or a combination of solubilized protease crystals and solubilized protease precipitate.

* * * * *